(12) United States Patent
Dessing

(10) Patent No.: US 12,201,079 B2
(45) Date of Patent: Jan. 21, 2025

(54) MILKING SYSTEM WITH DETECTION SYSTEM

(71) Applicant: LELY PATENT N.V., Maassluis (NL)

(72) Inventor: Jacobus Petrus Maria Dessing, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 993 days.

(21) Appl. No.: 17/273,856

(22) PCT Filed: Sep. 19, 2019

(86) PCT No.: PCT/NL2019/050619
§ 371 (c)(1),
(2) Date: Mar. 5, 2021

(87) PCT Pub. No.: WO2020/067881
PCT Pub. Date: Apr. 2, 2020

(65) Prior Publication Data
US 2021/0345576 A1    Nov. 11, 2021

(30) Foreign Application Priority Data

Sep. 24, 2018 (NL) ...................................... 2021686

(51) Int. Cl.
*A01J 5/013* (2006.01)
*G01N 1/10* (2006.01)
*G01N 1/18* (2006.01)
(Continued)

(52) U.S. Cl.
CPC .............. *A01J 5/0131* (2013.01); *G01N 1/18* (2013.01); *G01N 21/77* (2013.01); *G01N 21/85* (2013.01);
(Continued)

(58) Field of Classification Search
CPC .......... A01J 5/0131; A01J 5/007; A01J 7/022; G01N 1/18; G01N 2001/1093;
(Continued)

(56) References Cited

U.S. PATENT DOCUMENTS 4,850,817 A * 7/1989 Nason ................ A61M 5/14216
417/362
5,096,828 A    3/1992 Ishizaka et al.
(Continued)

FOREIGN PATENT DOCUMENTS

EP          626129 A1 * 11/1994 .............. A01J 7/022
JP       2005203437 A  *  7/2005
(Continued)

OTHER PUBLICATIONS

Masashi JP 2005-203437A translation (Year: 2005).*
(Continued)

*Primary Examiner* — Jennifer Wecker
*Assistant Examiner* — Jonathan Bortoli
(74) *Attorney, Agent, or Firm* — Birch, Stewart, Kolasch & Birch, LLP

(57) ABSTRACT

A milking system includes a device to sample and analyse a milk sample, including a control unit, a sample supply line connected to the milk line, a pump to control the sample flow, an optical radiation source, and an optical sensor device to detect and analyse optical radiation coming from the reagent pad with said sample, to provide an indication of a substance in the sample, a tape mover to move and unwind the tape from the tape reel, and a pump drive, external to the cassette, and releasably operably connected to the pump device for driving the pump device. The sampling and analysis device also includes a cassette with a sample receiving line, releasably connected to the sample supply line by a liquid connector, and arranged to receive the
(Continued)

Figure 1:
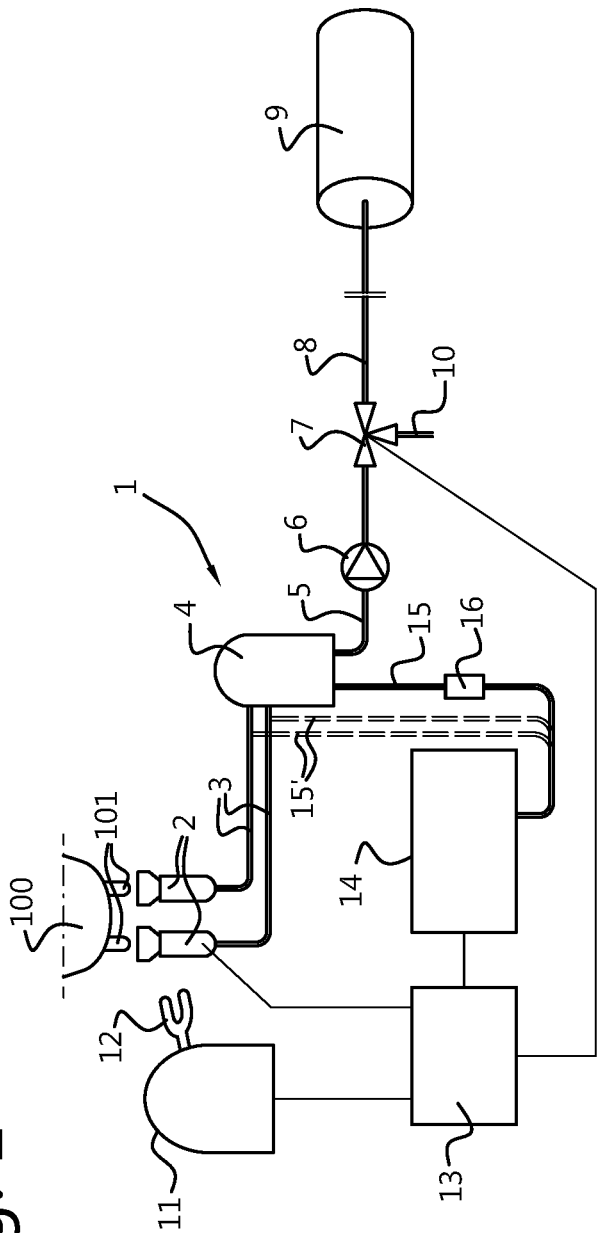

sample from the sample supply line, a tape reel with a tape that includes a base tape layer and a series of separate reagent pads, and a dosing device to provide a droplet of the sample onto a reagent pad. The dosing device includes a nozzle in fluid connection with the sample receiving line, and a nozzle mover arranged to move the nozzle in at least a longitudinal direction. The cassette is replaceably received in the milking system. Hereby, a large number of parts that are subject to wear and contamination by milk residues are exchanged regularly, which improves measurement reliability and accuracy.

13 Claims, 2 Drawing Sheets

(51) Int. Cl.
G01N 21/77 (2006.01)
G01N 21/85 (2006.01)
G01N 33/04 (2006.01)
G01N 35/00 (2006.01)

(52) U.S. Cl.
CPC ....... G01N 33/04 (2013.01); G01N 35/00009 (2013.01); G01N 2001/1093 (2013.01); G01N 2001/185 (2013.01)

(58) Field of Classification Search
CPC ............. G01N 2001/185; G01N 21/77; G01N 21/85; G01N 33/04; G01N 35/00009; G16B 20/00; G16B 20/20; G16B 20/40; G16B 30/00
See application file for complete search history.

(56) References Cited

U.S. PATENT DOCUMENTS

| | | | | |
|---|---|---|---|---|
| 5,846,064 | A * | 12/1998 | Refson | ................ F04B 43/082 417/474 |
| 2002/0124803 | A1* | 9/2002 | Chen | ..................... A01K 1/12 119/14.08 |
| 2009/0050061 | A1* | 2/2009 | Duke | ..................... A01J 7/04 119/14.08 |
| 2010/0261611 | A1* | 10/2010 | Peters | ............... G01N 35/1002 506/7 |
| 2014/0151308 | A1* | 6/2014 | Kelly | .................. G01N 17/008 210/141 |
| 2015/0086997 | A1* | 3/2015 | Linder | ............. B01L 3/502738 435/7.1 |

FOREIGN PATENT DOCUMENTS

| | | |
|---|---|---|
| WO | WO 02/069697 A1 | 9/2002 |
| WO | WO 2004/034063 A2 | 4/2004 |
| WO | WO 2004/034063 A3 | 4/2004 |
| WO | WO 2012/087235 A1 | 6/2012 |

OTHER PUBLICATIONS

International Search Report, issued in PCT/NL2019/050619, PCT/ISA/210, dated Feb. 17, 2020.
Written Opinion of the International Searching Authority, issued in PCT/NL2019/050619, PCT/ISA/237, dated Feb. 17, 2020.

* cited by examiner

MILKING SYSTEM WITH DETECTION SYSTEM

The present invention relates to a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the animal's management, in particular the milking of the animal, based on a result of said analysis, wherein the sampling and analysis device comprises a control unit for controlling the sampling and analysis device, a sample supply line connected to the milk line and arranged to receive, under the control of the control unit, said sample from the milk line, a tape reel with a tape wound on said tape reel, which tape comprises a base tape layer to which is provided a series of separate reagent pads that are arranged to provide a detectable response in the presence of at least one substance, a dosing device arranged to provide, under the control of the control unit, a droplet of the sample onto a reagent pad, the dosing device comprising a nozzle in fluid connection with the sample receiving line, and a pump device that is controlled by the control unit and that is arranged to control the flow of the sample to the nozzle, a tape mover, arranged to move and unwind the tape from the tape reel, under the control of the control device, an optical radiation source for emitting optical radiation, and an optical sensor device arranged to detect optical radiation coming from the reagent pad supplied with said droplet of the sample, and to analyse the detected optical radiation to provide an indication of a presence or concentration of said at least one substance in said droplet.

Document WO02069697A1 discloses such a system. A problem of this known system is that operating reliably for a long time with unfiltered milk straight from the dairy animal and in barn environment proves difficult.

It is an object of the present invention to provide a system of the kind indicated above, that is better able to operate reliably for a long time even with milk and in a barn environment.

The present invention achieves at least one of the above objects by means of a milking system, in particular a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the animal's management, in particular the milking of the animal, based on a result of said analysis, wherein the sampling and analysis device comprises a control unit for controlling the sampling and analysis device, a sample supply line connected to the milk line and arranged to receive, under the control of the control unit, said sample from the milk line, a pump device that is arranged to control the flow of the sample, a cassette with a sample receiving line, releasably connected to the sample supply line by means of a liquid connector in the cassette, the sample receiving line being arranged to receive the sample from the sample supply line, a tape reel with a tape wound on said tape reel, which tape comprises a base tape layer to which is provided a series of separate reagent pads that are arranged to provide a detectable response in the presence of at least one substance, a dosing device that is controlled by the control unit and is arranged to provide a droplet of the sample onto a reagent pad, the dosing device comprising a nozzle in fluid connection with the sample receiving line, a nozzle mover arranged to move the nozzle in at least a longitudinal direction, and a pump device that is arranged to control the flow of the sample to the nozzle, a tape mover, arranged to move and unwind the tape from the tape reel, under the control of the control device, an optical radiation source for emitting optical radiation, and an optical sensor device arranged to detect optical radiation coming from the reagent pad supplied with said droplet of the sample, and to analyse the detected optical radiation to provide an indication of a presence or concentration of said at least one substance in said droplet, further comprising a pump drive, that is external to the cassette, and that is releasably operably connected to the pump device for driving the pump device, wherein the cassette is replaceably received in the milking system.

Both the environment with harmful gases such as ammonia and nitrous oxide, and unfiltered milk straight from the cow are a heavy burden on many parts of the sensitive sampling and analysis system. Therefore, good cleaning is required to maintain accurate and reliable measurements. However, all this cleaning, with in turn aggressive substances such as acids, lye and even hot water, also causes wear to the system. In the mid to long term, degradation can hardly be prevented, or at least only at very high cost. The insight of the inventors of the present invention is that a number of parts that are particularly vulnerable to soiling or wear by the milk, the environment and/or by the cleaning, in particular but not exclusively the greater part of the dosing device, are made replaceable together with the tape with the reagent pads, the latter being replaceable anyway. This prevents that wear parts are used for a too long time, which could otherwise lead to inaccurate measurements or even failure of the system. It also minimises maintenance, since exchanging the cassette has to take place anyway after a certain, fixed number of samplings. By exchanging the cassette, a number of vulnerable parts are exchanged at the same time.

In the present invention, the milking control device is arranged to control the animal's management, in particular the milking of the animal, based on a result of said analysis. In some embodiments, this means that a part of the milk, in particular the foremilk, is sampled and analysed, and the results are used to control the destination of the milk: if the results indicate that the milk is fit for human consumption, it may be led to the bulk milk tank, and if not, the milk should be separated. In other Alternatively or additionally, controlling the milking comprises sampling and analysing a representative part of the main milk, i.e. during all of the milking. If then the analysis results can be made available in-line, the results may still be used to control the destination of the milk, but if it takes too long, such as more than one minute, the results could also be used in a subsequent milking or otherwise. In other words "milking" comprises in general any present or future milking turn of the animal. Additional ways of controlling the milking comprise setting milking parameters based on (preferably in-line) analysis results, such as stopping milking if a fat content of the milk achieves a certain threshold value. Still other uses of the analysis results are available, such as adjusting feeding of the animal. If the milk shows a fat:protein ratio that deviates from a target for the animal, such as about 1.1-1.2 for Holstein cows, then the composition of the feed should be adjusted. These uses are not deemed to be limiting.

It is furthermore noted that the tape mover may be a motor, that is driven under the control of the control unit, in the same way that a musicassette is driven by the motor. In most cases, the tape will be unwound from the tape reel and onto a collector reel, or bobbin. In such a case it will be the collector reel, or bobbin, that is driven by the motor. In most cases, the motor will be external to the cassette, with only a releasable connection between the tape reel and the motor, again as in a musicassette player.

The milking means may be conventional, in which the teat cups are attached to the teats manually, or they may be robotic, in which the teat cups are attached by means of a robot arm, thus requiring no human supervision at all. In the latter case, a reliable functioning according to the present invention is of additional value.

The sample receiving line is releasably couplable to the sample supply line of the milking system, by means of a liquid connector in the cassette. This means that there is a liquid connector, such as the ones used in water dispensers with an exchangeable water tank and so on. Thus, the sample may then flow from the milk line, via the sample supply line to the sample receiving line and then to the nozzle, where it may be supplied to reagent pad.

Particular embodiments, as well as features and advantages, are described in the dependent claims and the now following part of the description.

In embodiments, the pump device comprises a pump drive external to the cassette, as well as a pumping mechanism that is provided in the cassette and is drivable by the pump drive. In this embodiment, the pumping mechanism is also provided in the cassette, and therefore exchanged upon exchanging the cassette. Since this mechanism will also be subject to deterioration through wear and soiling, it is advantageous for the reliability and accuracy that this mechanism is exchanged after a number of samplings. The pump drive is in principle only the motor of the pumping mechanism, and is not subjected to clean, ui.e. much less wear. The pumping mechanism is operably connectible to the pump drive by any means, such as a mechanical or electromagnetical coupling.

In embodiments, the pumping mechanism comprises a peristaltic pump, comprising a driveable protrusion, such as a rotor, for moving liquid of the sample through the sample receiving line. Such pumps are easily controllable, can dose very small amounts, and can serve as a valve to open or close off the sample line. Yet, other pumping mechanisms are not excluded, such as piston pumps or diaphragm pumps.

In embodiments, the control unit is arranged to drive the pump device with the pump drive in three stages, comprising a first stage in which the sample receiving line, from a closed situation, is opened by the protrusion, a second stage in which the protrusion moves liquid through the sample receiving line towards the nozzle, and a third stage in which the protrusion meters out liquid onto a reagent pad. These stages are useful, in that in the first and second stage it is possible to clean the line with milk, in particular first milk from the sample, in order to flush out any milk residues from a previous sample. The third stage is for dosing a preferably exactly known amount of liquid onto a reagent pad.

In embodiments, the pump drive comprises a caromed wheel, in particular a stepper motor with a cammed wheel, and wherein the cassette comprises a connector that is coupled to the protrusion and is driveable by the cammed wheel. Such a cammed wheel, with one or more cams, is a very simple, robust and reliable means of controlling the pump mechanism, that features the possibility of a programmed sequence of steps, depending on the layout of the cam(s) and of course of the pumping mechanism that is releasably coupled to the cammed wheel. A number of different movements may thus be carried out by the pumping mechanism under the working of the caromed wheel. Yet, other pump drives are not excluded, such as electromagnetic drives such as in magnetic stirrers, and so on.

In embodiments, the cassette further comprises an internal cassette flushing liquid line with a liquid connector for connection to an external flushing liquid line. The flushing line is provided to aid in cleaning the milk carrying lines. Thereto, the internal cassette flushing liquid line is connectible to the milk carrying sample receiving line and thus to the nozzle. A separate flushing liquid, or any other liquid such as cleaning liquid, may then be sent through the internal cassette flushing liquid line. Possible liquids are water, ho, tepid or cold, with or without additional cleaning agents such as acid, lye or disinfectant. It will also be clear that having this flushing liquid line in the cassette also helps in improving the reliability of the system, in that this line, too, is subject to wear and tear. Furthermore, it is noted that such a flushing liquid line is not necessary, for example if the sample supply line and sample receiving line are (always) cleaned via the milking system, that cleans the milk line as well.

In embodiments, the nozzle is, when in use, arranged and positioned to supply said droplet upwardly, and the cassette further comprises a cup extending around the nozzle, that is arranged to collect, by means of gravity, liquid ejected by the nozzle, the cup comprising a drain line with a drain liquid connector for connection to an external drain liquid line. The cassette is preferably gas tight, in order to protect the reagent pads against the influence from the environment, in particular harmful gases mentioned above, and even more in particular moisture, that affects many of the useful reagents. By providing a cup around the nozzle, ejected liquid that is not taken up by the reagents may be caught and collected, because gravity pulls it downward, and thus away from the nozzle and the reagent pad. This surplus ejected liquid is subsequently drained from the cup. This helps in keeping the cassette's inside clean and prevents moisture from building up in the cassette.

The cup comprises a bottom part extending sidewardly from the nozzle or an end part of the sample receiving line towards the nozzle, and further a wall part extending around the nozzle, the bottom part and the wall part together forming a fluid collecting space around the nozzle. The drain line is connected to the cup in the bottom part thereof.

In embodiments, the cassette comprises a housing of an optically opaque material, as well as a window that is transmissive to the radiation from the reagent pad. As mentioned above, the cassette is preferably gastight. It is also preferably light-tight, in order to prevent undesired influences on reagents, in particular before or during a reaction with a sample. In that case, the cassette has a housing of an opaque material, wherein "opaque" means that it blocks at least the optical radiation emitted by the optical radiation source, in particular any optical radiation for which the optical sensor is sensitive. The window is then provided to allow the optical radiation from the reagent pad to reach the detector. Preferably, the sampling and analysis device comprises a shutter to shut off the window under the control of the control unit. This further reduces any negative influence of incoming optical radiation on the reagents.

The invention also relates to a cassette for use in the system of the invention, and comprising a sample receiving line, releasably connected to the sample supply line by means of a liquid connector in the cassette, the sample receiving line being arranged to receive the sample from the sample supply line, a tape reel with a tape wound on said tape reel, which tape comprises a base tape layer to which is provided a series of separate reagent pads that are arranged to provide a detectable response in the presence of at least one substance, and a dosing device arranged to provide, under the control of the control unit, a droplet of the sample onto a reagent pad, the dosing device comprising a nozzle in fluid connection with the sample receiving line, and a pump device that is controlled by the control unit and that is arranged to control the flow of the sample to the nozzle. Such cassettes may be filled with tape with one or more series of reagent pads. If filled with a tape with one type of reagent pads, it is advantageous that the cassettes may be exchanged, in that different types may be used alternately.

It is expressly noted that all embodiments described above for the milking system of the present invention in which one or more features relate to the cassette itself may also be applied in the cassette according to the invention, with corresponding advantages and uses.

The invention also relates to a milking apparatus, comprising a docking station for operably and releasably receiving at least one cassette according to the invention, such as to form together a milking system according to the invention. Such a milking apparatus is ready to be used with a cassette according to the invention, and can then achieve the advantages and uses as described for the milking system according to the invention.

Figure 2:
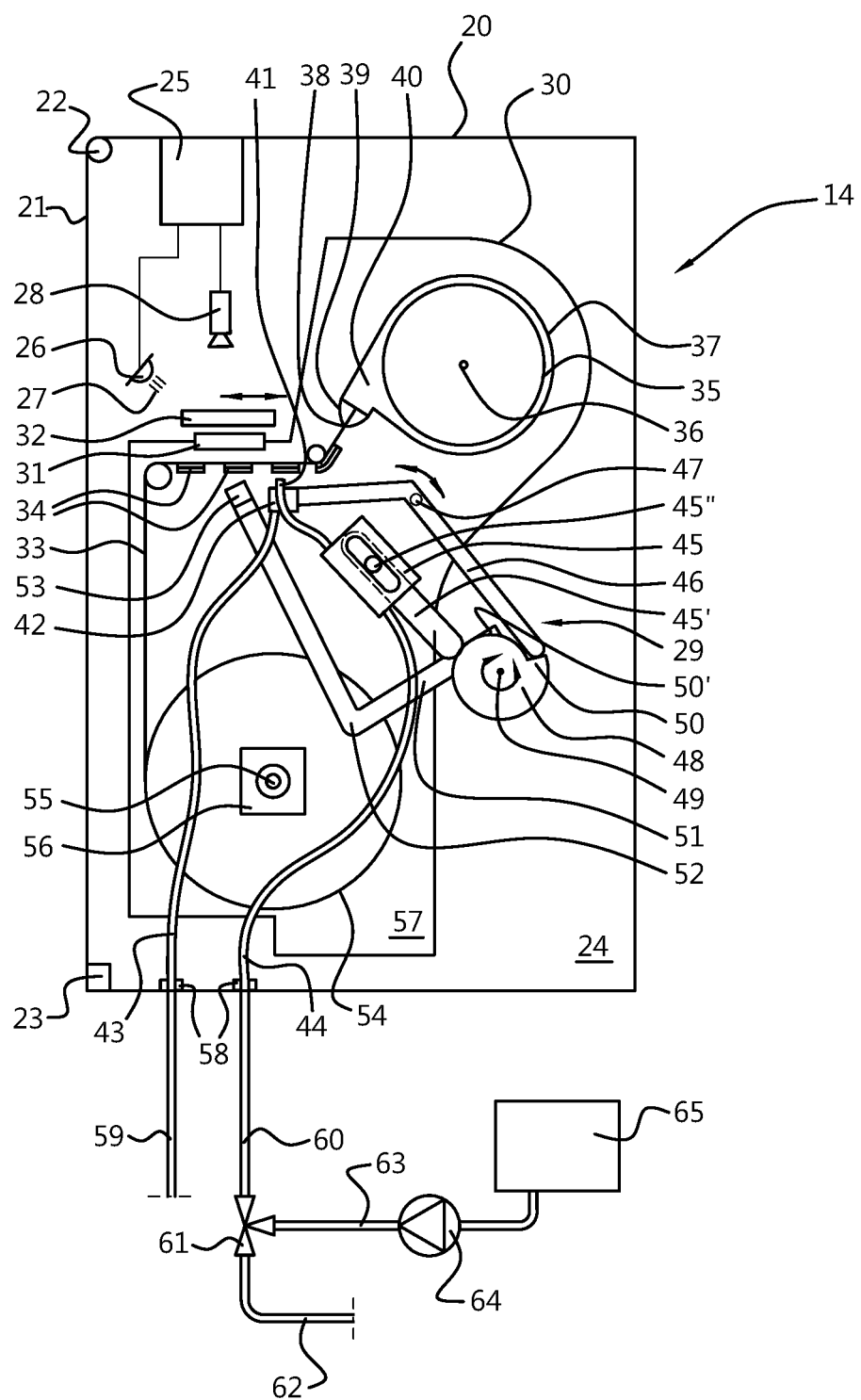

The invention will now be explained further by means of a number of embodiments described below and in the drawings, in which:

FIG. 1 shows a diagrammatic representation of a milking system according to the present invention; and FIG. 2 shows a diagrammatic representation of a sampling unit as in the milking system according to the present invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 15. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on.

FIG. 2 shows a diagrammatic representation of a sampling unit 14 as in the milking system according to the present invention. The sampling unit 14 has a box 20 with a lid 21 that hinges around a hinge 22 and is locked with a lock 23, and with an in-box space 24. In the box 20 there are provided a sampler control unit 25, a light source 26 emitting light 27, a camera 28, a drive 29 and a cassette 30.

The cassette 30 has a window 31, that can be covered with a shutter 32, and through which a tape 33 with reagent pads 34 may be observed. The tape 33 is wound from a supply reel 35, rotatable around an axle 36 in a subhousing 37, that has an exit opening 38 closed by means of a seal 39 and that surrounds an internal subhousing space 40. A nozzle is denoted by 41, is partly surrounded by an overflow cup 42 with a housing drain line 43, and is itself connected to a housing supply line 44, which is controlled by a sample pump 45.

The drive 29 comprises a nozzle mover arm 46, which is hingeably driveable around a hinge 47 by a first cam wheel 48, which in turn is rotatably driven around an axle 49 by non-shown cam wheel drive and which has a first cam 50. The drive 29 also comprises a pump drive arm 45', which drives a moveable pump element 45". The drive 29 also comprises an rinsing cup mover arm 51 that is driveable around a hinge 52 by a second cam 50', and that at its end carries a rinsing cup 53.

The used tape is collected around a collecting reel 54 that is driveable around an axle 55 by means of a tape drive 56. The inner housing space is denoted by 57. Liquid connectors 58 supply connections for an external drain line 59 and an external supply line 60, the latter being connectible, via valve device 61, to a milk sampling line 62, such as the sampling line 15 of FIG. 1, as well as a cleaning fluid supply line 63, that supplies cleaning fluid via a supply pump 64 from a reservoir 65.

The sampling unit 14 as shown here comprises a substantially light- and airtight box 20, with a number of fixed parts and a replaceable cassette, or housing, 30 with a number of parts that are replaced each time the cassette 30 is replaced. As explained above, and according to the invention, this ensures that parts that are susceptible to wear and contamination, such as milk carrying parts, are exchanged regularly.

In the embodiment of FIG. 2, the cassette or housing 30 may be exchanged by unlocking the lock 23, such as by turning a key, shifting a bolt or the like, subsequently opening the lid 21 around the hinge 22, taking out the used cassette 30 and replacing it with a new and unused cassette. The fluid connections 58 between housing drain line 43 and the external drain line 59, and between the housing supply line 44 and the external supply line 60, respectively are made, either manually or automatically by placing the cassette 30. The various arms 45', 46, 51 driveable by the drive 29 are in an idle position in which they come to rest against respective cams, two of which are shown here as the first and second cams 50, 50', respectively. Thereafter the sampling unit 14 is closed again. It is noted that other means of moving the nozzle and/or the rinsing cup, instead of the mover arms 45', 46 and 51 may be used, such as pneumatic means, that can be connected via gas tubes and fluid connectors, connectible like the drain and supply lines, and controllable via gas pumps, or any other suitable means.

In use, a sample of milk is supplied through the milk sampling line 62, such as from the milk jar 4 in FIG. 1, and via the valve device 61 and the external supply line 60, a fluid connector 58, the housing supply line 44 the sample pump 45 and the nozzle 41. Thereto, the sample pump is put in an open position by means of the moveable pump element 45", driven by the pump drive arm 45' under the control of the drive 29, in turn controlled by the sampler control unit 25. It is noted that the sampler control unit is a part inside the box 20, and separate from the robot control unit 13 in FIG. 1. It is also possible that the sampler control unit is provided outside the box 20, still as a separate part, or even as an integral part of the robot control unit 13. It is furthermore noted that use may be made of a flat wall part, as provided in the rinsing cup 53, to control sample drop formation. The cup 53 is open towards the bottom, for receiving the nozzle 41, if desired together with the overflow cup 42 surrounding it. By inserting the nozzle in the rinsing cup, the nozzle may be rinsed by ejecting (cleaning or other) liquid through the nozzle, which liquid is shielded by the rinsing cup, and subsequently collected in the overflow cup, and then drained via drain line 43/59.

The sample pump 45 may be any suitable pump such as a peristaltic pump. The latter has an advantage in that it is easily closable, such as by pressing the moveable pump element against an abutment surface, and is accurately controllable for dosing small amounts, such as a droplet of sample onto a reagent pad. Nevertheless, other types of pumps that can provide good dosing control are not excluded.

A droplet of the sample is thus provided by the nozzle 41 on a reagent pad 34. These reagent pads 34 are provided as a series of consecutive pads on a tape 33, and provide a detectable response in the presence of a (detectable) amount of to-be-detected substance in the milk sample. For example, the reagent pad 34 may show a colouring in the presence of progesterone in the milk sample, the intensity of speed of the colouring depending on the concentration of the progesterone. of course, other substances may also be used. The response, or absence thereof, is detected by means of a camera 28 that images, through a window 31 in the box, radiation coming from the reagent pads 34. This radiation is either radiation 27 that was emitted by the light source 26, and then reflected or scattered by the reagent pad 34, or may be radiation of a different type, generated by a reaction in the reagent to the radiation 27 from the light source 26, such as a fluorescence reaction. The light source 26 may emit optical radiation, such as visible light, UV(A) radiation or (near) infrared light, and is selected suitable, such as from corresponding LEDs or other. The window may optionally be covered by means of a shutter 32 that is movable in the direction of the double arrow, in order to protect the contents of the cassette 30, and in particular the tape 33 with the reagent pads 34, against any negative influences of the radiation.

After the nozzle 41 supplies a droplet of the milk sample to a reagent pad 34, the camera 28 observes the pad, and detects any response. Thereto, the pad 34 is first moved by means of the tape mover 56 that advances the tape 33 a bit. This not only frees up a subsequent pad 34, but also moves the pad to the field of view of the camera 28. Note that it is also possible, and in fact preferred, that that field of view is where the sample droplet is provided by the nozzle 41. That allows to observe the response in the reagent pad immediately. Also, the new unused pad can stay in a protected environment for as long as possible. Preferably, the field of view of the camera 28 contains more than one reagent pad 34. This allows a reagent pad to stay in view for more than the average milking/sampling time. For dairy cows and sampling every cow, this time may be as short as a few minutes. Such a short time requires a relatively high dose of reagent in the reagent pads. This is not necessary if the reagent pad stays in view for a longer time, such as double or triple the time, which can be achieved by having two or three reagent pads in view of the camera 28. Of course, other numbers are possible as well, although very high numbers reduce the amount of visual information that the camera 28 may extract from each individual reagent pad 34.

After assessment by the camera 28, the tape 33 with the now used reagent pads is pulled further forward by the tape mover 56, and is eventually rolled onto the collecting reel 54. The tape mover 56 may in principle be any kind of motor for turning the collecting reel 54, such as a motor from a cassette deck, or a stepper motor. However, it is also possible to move the collecting reel 54 by means of a non-shown mover arm that is coupled to another of the cam wheels (also not shown here). The system follows more or less the implementation of the moving of the arms 46 and 51. This further allows the tape mover 56, a moving part, and thus a wear-part, to be exchangeable by exchanging the cassette. However, this is not necessary according to the present invention. It is stressed here that the combination of on the one hand providing a relatively large number of parts in the cassette, which is replaceable, thereby replacing all those parts, and on the other hand some external drive means for those moveable parts that are each time exchanged provides for advantages according to the invention. In the embodiment shown, not only the tape reels with the tape are exchangeable, which is of course necessary, but also the nozzle 41 with the final part of the connected sample line, the greater part of a pump means 45-45", as well as optional parts such as the rinsing cup 53.

A tape 33 may comprise more than one type of reagent pad 34. The reagents for such reactions are often enzymes or other biologically active substances. Very often, these are quite sensitive to moisture, that can affect their properties. For example, moisture alone may lead to a colour reaction, which is of course undesirable because it is meaningless. It may also lead to a different sensitivity of the reagent, which deteriorates the accuracy of the measurement. For these and other reasons, it is advantageous that the presence of moisture is prevented and suppressed as much as possible.

Moisture is suppressed by a number of possible measures. First of all, and obviously, the box 20 is made as airtight as possible, so that moisture may in principle only be provided by air in the in-box space 24, the volume of which can be kept small. It is furthermore possible to provide moisture absorption inside the box 20, such as by means of an absorptive lining or by means of packages of absorbers such as silica gel or the like. However, because the box 20 is in principle a permanent part of the sampling unit of the milking system, such liners will inevitable become moisture saturated and thus ineffective, while the same holds for the absorber packages, that in the end will need replacement, which represents an undesirable human intervention if it can be prevented.

The cassette 30 in which the tape is provided need never have a higher (relative) humidity than the in-box space 24. Nevertheless, some moisture may seep through the box wall, because there will always be connections, either permanent or temporary. But more importantly, sampling inherently brings moisture into the cassette 30. Thus, measures to suppress moisture inside the cassette 30 are desirable as well. Thereto, for example, the supply reel 35 with the part of the tape 33 with unused reagent pads 34 is provided in a subhousing 37. The tape 32 exits the subhousing via an exit opening 38 that is sealed by means of e.g. a duckbill seal 39 or other suitable seal. This ensures that moisture from the inner housing space 57 will only very slowly enter the internal subhousing space 40. Since the tape 33 with the reagent pads 34 can, and will, be produced in a very dry environment, the air in the subhousing 37 can have an extremely low (relative) humidity of, say, only a few %. Depending on the quality of the duckbill, the low humidity need rise only very slowly.

In order to further suppress moisture, the supply reel 35 itself may be provided with a desiccant. For example, the supply reel 35 is substantially made of a material with desiccant properties, which means that it is able to actively remove water from the surrounding air. This further ensures that the humidity inside the subhousing 37, thus at the unused reagent pads 34, remains at a suitable level, such as a few %, for an even longer time. And since the supply reel 35 may take up a substantial volume within the subhousing 37, depending on the ratio between the fully wound tape and the diameter of the supply reel 35, the total moisture absorption capacity may be very high. The moisture absorption properties depend on the material used. Preferably, the material is a compound material, comprising at least a true desiccant/moisture absorber/adsorber, and a matrix to provide sufficient strength to the supply reel 35. A useful example is marketed by the company Capitol Specialty Plastics, Inc., for example for its Active-Vial™ M3003 series. Yet, it is also possible to have the (true) desiccant material mainly at the surface of the supply reel 35. For example, in cases where the supply reel 35 is used for a relatively short time only, it may be better to have a high speed of absorption, with less total absorption capacity.

Yet a further optional measure is to have the collecting reel 54 also comprise desiccant material at least at its surface. Optionally, the collecting reel 54 is also substantially made of desiccant material, in much the same way as described above for the supply reel 35. Note that providing a subhousing 37 is not necessary, although advantageous, especially if the collecting reel 54 is also provided with, or from, desiccant material, since then there is a very large moisture absorption capacity and/or speed from both reels 35 and 54.

The above described embodiments only serve to help explain the invention without limiting this in any way. The scope of the invention is rather determined by the appended claims.

The invention claimed is:

1. A milking system comprising a milker including a milking control device the milker arranged for milking milk from a dairy animal, a milk line fluidly connected to the milker, and a sampling and analysis device arranged to take a sample of the milk from the milk line and to analyse the sample,
   wherein the milking control device is arranged to control a management of the dairy animal based on a result of an analysis of the sample, wherein the sampling and analysis device comprises
   a control unit for controlling the sampling and analysis device;
   a sample supply line connected to the milk line and arranged to receive, under the control of the control unit, said sample from the milk line;
   a pump arranged to control a flow of the sample; and
   a cassette including
      a first liquid connector,
      a sample receiving line releasably connected to the sample supply line by the first liquid connector in the cassette, wherein the sample receiving line is arranged to receive the sample from the sample supply line
      a tape reel including a tape wherein the tape is wound around said tape reel, the tape comprising a base tape layer to which a series of separate reagent pads are arranged to provide a detectable response to at least one substance, and
      a dosing device controlled by the control unit and arranged to provide a droplet of the sample onto a reagent pad of the series of separate reagent pads, the dosing device comprising a nozzle fluidly connected to the sample receiving line and a nozzle mover arranged to move the nozzle in at least a longitudinal direction;
   the sampling and analysis device further comprising a tape mover arranged to move and to unwind the tape from the tape reel under the control of the milking control device;
   an optical radiation source for emitting optical radiation;
   an optical sensor arranged to detect optical radiation from the reagent pad supplied with said droplet of the sample, and to analyse the detected optical radiation to provide an indication of a presence or of a concentration of said at least one substance in said droplet, droplet; and
   a pump drive external to the cassette and releasably operably connected to the pump device for driving the pump device,
   wherein the cassette is replaceably received in the milking system, and
   wherein the control unit is arranged to drive the pump with the pump drive in three stages comprising a first stage in which the sample receiving line is opened from a closed state to an open state by a protrusion, a second stage in which the protrusion moves a liquid through the sample receiving line towards the nozzle, and a third stage in which the protrusion meters out the liquid onto a reagent pad of the series of separate reagent pads.

2. The milking system according to claim 1, wherein the pump comprises a pump drive external to the cassette and wherein the cassette further comprises a pumping mechanism provided in the cassette and drivable by the pump drive.

3. The milking system according to claim 2, wherein the pumping mechanism comprises a peristaltic pump comprising the protrusion for moving a liquid of the sample through the sample receiving line.

4. The milking system according to claim 1, wherein the pump drive comprises a cammed wheel, and wherein the cassette further comprises a connector coupled to the protrusion and driveable by the cammed wheel.

5. The milking system according to claim 1, wherein the cassette further comprises an internal cassette flushing liquid line including a second liquid connector for connecting the internal cassette flushing liquid line to an external flushing liquid line.

6. The milking system according to claim 1, wherein in use the nozzle is arranged and positioned to supply said droplet upwardly, and wherein the cassette further comprises a cup extending around the nozzle, arranged to collect, by means of gravity, a liquid ejected by the nozzle, the cup comprising a drain line including a drain liquid connector for connecting the drain line to an external drain liquid line.

7. The milking system according to claim 1, wherein the cassette comprises a housing of an optically opaque material and a window transmissive to the detected optical radiation from the reagent pad of the series of separate reagent pads, the sampling and analysis device further comprising a shutter to shut off the window under the control of the control unit.

8. The milking system according to claim 2, wherein the pumping mechanism comprises a peristaltic pump comprising the protrusion for moving liquid of the sample through the sample receiving line.

9. The milking system according to claim 2, wherein the pump drive comprises a cammed wheel, and wherein the cassette comprises a connector coupled to the protrusion and driveable by the cammed wheel.

10. The milking system according to claim 3, wherein the pump drive comprises a cammed wheel, and wherein the cassette comprises a connector coupled to the protrusion and driveable by the cammed wheel.

11. The milking system according to claim 2, wherein the cassette further comprises an internal cassette flushing liquid line including a liquid connector for connecting the internal cassette flushing liquid line to an external flushing liquid line.

12. The milking system according to claim 3, wherein the cassette further comprises an internal cassette flushing liquid line including a liquid connector for connecting the internal cassette flushing liquid line to an external flushing liquid line.

13. The milking system according to claim 4, wherein the cassette further comprises an internal cassette flushing liquid line including a liquid connector for connecting the internal cassette flushing liquid line to an external flushing liquid line.

* * * * *